United States Patent [19]

Slagle

[11] Patent Number: 4,802,465

[45] Date of Patent: Feb. 7, 1989

[54] RECLINING TRACTION LOUNGE

[76] Inventor: Bernie L. Slagle, 29 Allenwood Estates, Vincentown, N.J. 08088

[21] Appl. No.: 808,759

[22] Filed: Dec. 13, 1985

[51] Int. Cl.[4] .............................................. A61F 5/00

[52] U.S. Cl. ...................................... 128/71; 269/328; 128/75

[58] Field of Search .................... 128/70, 71, 69, 25 R, 128/75; 5/431, 432, 433, 443, 62; 269/322, 323, 328

[56] References Cited

U.S. PATENT DOCUMENTS

| | | | |
|---|---|---|---|
| 2,553,969 | 5/1951 | Hien et al. | 128/71 X |
| 3,118,442 | 1/1964 | Montgomery | 128/71 |
| 3,315,667 | 4/1967 | Yoder | 128/71 X |
| 4,103,681 | 8/1978 | Shanley | 128/71 |
| 4,405,128 | 9/1983 | McLaughlin et al. | 128/25 R X |

FOREIGN PATENT DOCUMENTS

| | | | |
|---|---|---|---|
| 185229 | 4/1906 | Fed. Rep. of Germany | 128/71 |
| 88820 | 2/1967 | France | 128/71 |
| 359835 | 3/1962 | Switzerland | 128/71 |
| 208883 | 1/1924 | United Kingdom | 128/71 |

*Primary Examiner*—Edgar S. Burr

*Assistant Examiner*—Moshe I. Cohen

*Attorney, Agent, or Firm*—Norman E. Lehrer

[57] ABSTRACT

A reclining traction lounge includes an inclined support surface for supporting a person's buttocks, back, shoulders and head. The support surface is mounted for limited front and back movement on a downwardly inclined frame. A pawl movable with the support surface engages a stop carried by the frame to prevent rearward movement of the support surface. The frame also carries a knee support which is located adjacent the forward end of the movable support surface. The portion of the support surface adjacent the knee support which is adapted to underlie the person's buttocks is relatively slippery whereas the portion of the support surface which underlies the person's shoulders and head is padded and covered with a non-slip material. In use, a person reclines on the lounge with his lower legs hanging over the knee support and his back on the inclined support surface. As the pawl is lifted to disengage the stop, the support surface moves rearwardly and downwardly along the frame. The shoulders and head, lying on the non-slip material, move rearwardly, while the buttocks slide on the slippery surface. The back is, thus, put into traction.

10 Claims, 3 Drawing Sheets

RECLINING TRACTION LOUNGE

BACKGROUND OF THE INVENTION

The present invention is directed toward a traction device and more particularly toward a reclining traction lounge which is comfortable and relaxing for a patient but which provides adequate traction for his back.

Various devices have been proposed in the past for stretching a person's back or otherwise placing the same in traction. In one type of such device, the person utilizing the same is reclining on an inclined board with his feet above the level of his head and held in a strap or ankle fastener or the like. Examples are shown in U.S. Pat. Nos. 2,738,975 and 3,081,085. A similar arrangement is shown in U.S. Pat. No. 4,103,681 although in this case, the ankles or feet are not held by a strap. Rather, the knees are bent over a knee support which holds the lower part of the body.

These prior art devices are capable of providing traction to a person's back. However, it is relatively difficult for a person to get on and off of the same. Furthermore, because the person's feet are elevated well above his head, the person may be under a great deal of discomfort from the blood rushing to his head and, thus, cannot stay in the required position for an extended period of time.

U.S. Pat. No. 2,693,796 shows another type of traction device where the person utilizing the same is lying in a substantially horizontal plane. With this device, the person's feet are held in one end of a divided table and his chest is strapped onto the other end of the table. A crank is utilized to spread the two table halves apart thereby placing the person's spine under traction. Obviously since the person utilizing this device is strapped in place, a second person is needed to operate the equipment, thus making it unsuitable for a person to utilize by himself at home.

A similar type device having the crank located in a position wherein the person can operate it himself is shown in U.S. Pat. No. 2,695,071. However, this device is relatively complex having a large number of cooperating and moving parts. Furthermore, in order to utilize the same for providing traction on a person's back, the person's legs are elevated well above his head thereby subjecting the same to the defects discussed above.

The device shown in U.S. Pat. No. 3,866,605 is not specifically designed for placing a person's back in traction. However, as will be seen from the description of the present invention hereinafter, there are some structural similarities between the device shown in this patent and Applicant's invention. Because of the arrangement shown in this patent, it is not actually possible to place the person's back in traction. Furthermore, when utilizing the patented device, the person's feet are, again, elevated well above his head, thus making the device unsuitable for extended periods of use.

SUMMARY OF THE INVENTION

The present invention is designed to overcome all of the deficiencies of the prior art devices discussed above. The reclining traction lounge of the invention includes an inclined support surface for supporting a person's buttocks, back, shoulders and head. The support surface is mounted for limited front and back movement on a downwardly inclined frame. A pawl movable with the support surface engages a stop carried by the frame to prevent rearward movement of the support surface. The frame also carries a knee support which is located adjacent the forward end of the movable support surface. The portion of the support surface adjacent the knee support which is adapted to underlie the person's buttocks is relatively slippery whereas the portion of the support surface which underlies the person's shoulders and head is padded and covered with a non-slip material. In use, a person reclines on the lounge with his lower legs hanging over the knee support and his back on the inclined support surface. As the pawl is lifted to disengage the stop, the support surface moves rearwardly and downwardly along the frame. The shoulders and head, lying on the non-slip material, move rearwardly, while the buttocks slide on the slippery surface. The back is, thus, put into traction.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

DETAILED DESCRIPTION OF THE PREFERRED EMBODIMENT

Figure 1:
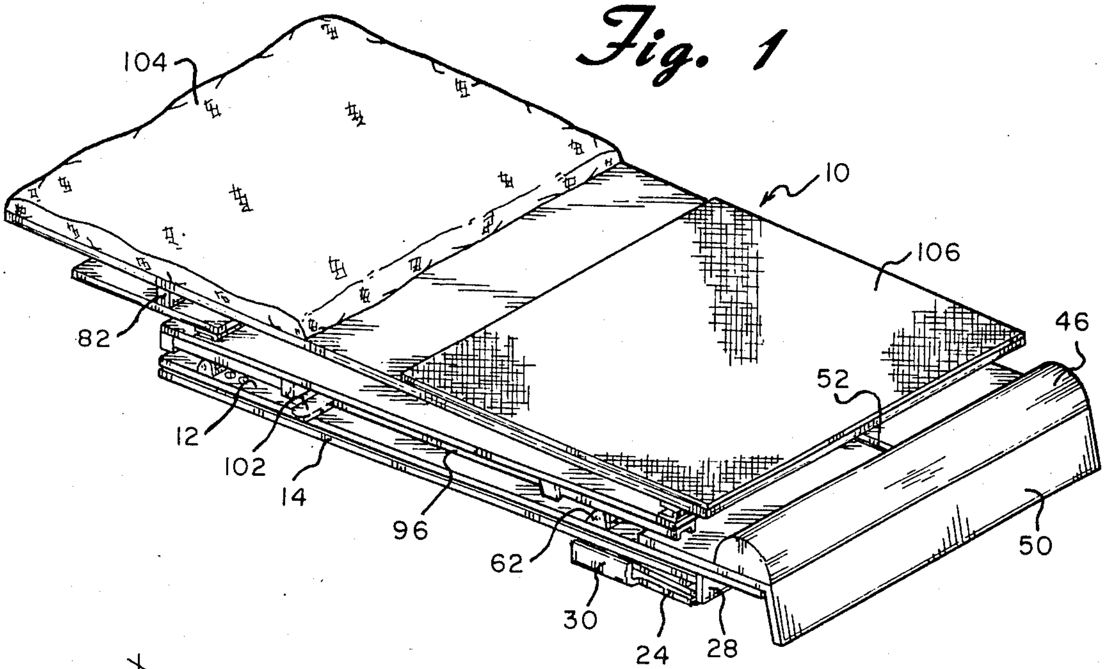
FIG. 1 is a perspective view of the reclining traction lounge constructed in accordance with the principles of the present invention but showing the same in an inoperative folded condition.
Figure 2:
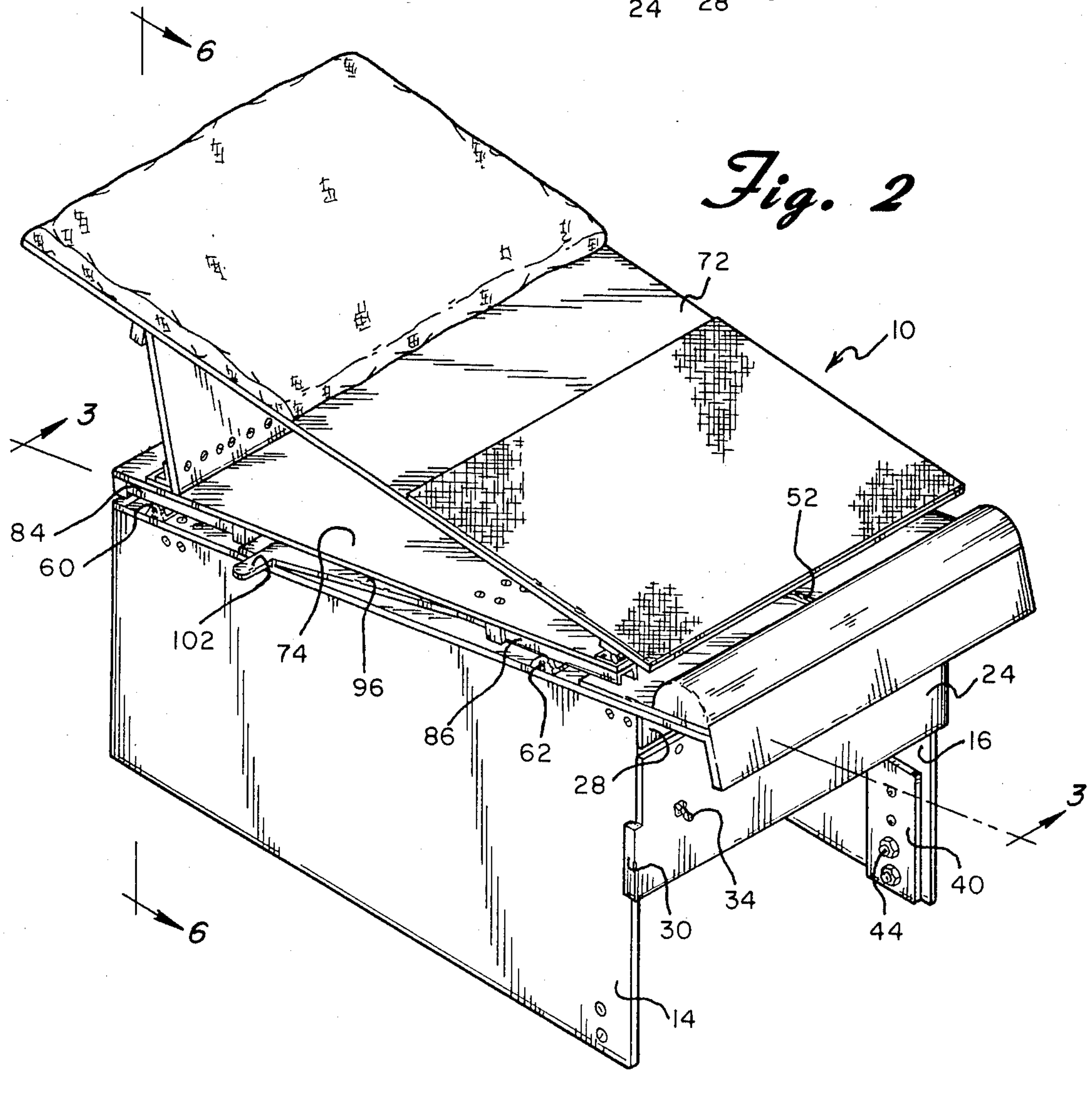
FIG. 2 is a view similar to FIG. 1 but showing the device in an operative position.

Referring now to the drawings in detail wherein like reference numerals have been used throughout the various figures to designate like elements, there is shown in FIGS. 1 and 2 a reclining traction lounge constructed in accordance with the principles of the present invention and designated generally at 10. FIG. 1 shows the lounge 10 in a collapsed condition whereby the same can be easily carried about from one place to the other. In FIG. 2, the lounge 10 is in its assembled operative condition.

The lounge 10 is comprised of a base or frame which includes an upper frame surface 12 and a pair of side walls 14 and 16. Left side wall 14 is hinged directly to the upper frame surface 12 so that when it is folded inwardly, it lies substantially flat against the lower surface thereof. As shown most clearly in FIG. 3, however, right side wall 16 of the frame is hinged through the use of hinges 18 and 20 to the downwardly extending partial wall 22. This provides a space for the left wall 14 to fold first and then right wall 16 to fold over the left wall 14.

A front wall 24 is also provided which is hinged at 26 to downwardly extending partial front wall 28. The partial wall 28 is low enough so that the front wall 24 can fold over the folded right and left side walls 14 and 16 as shown in FIG. 1. In order to maintian the frame in its erect condition, the side edges of the front wall 24 have projections such as shown at 30 which fit into corresponding recesses in the side walls 14 and 16. The front wall 24 is then tied to the side walls 14 and 16 through the use of ties 32 which attach to the inside of the side walls 14 and 16 and extend through openings in the front wall 24 where knots such as knots 34 and 36 can be formed.

When the frame is resting on a level floor or the like, the upper frame surface 12 is inclined downwardly from the front of the lounge to the back at an angle of between approximately 10° to 40° below the horizontal. However, this angle can be adjusted through the use of feet 38 and 40 which are attached to the lower end of the front of side walls 14 and 16. Each foot includes a plurality of holes passing therethrough such as the four holes 42 shown in foot 40. The side walls 14 and 16 have a pair of corresponding holes which can be aligned with any of the two adjacent holes 42 in the feet. When the proper holes are selected, bolts 44 maintain the feet in selected position. The foot 40 shown in solid lines in FIG. 3 might, for example, create an incline of approximately 20° in the slope of the upper frame surface 12. In the first downward position of the foot 40 shown in phantom in FIG. 3, the slope of the upper frame surface 12 may be at 25° and in the lowermost position shown in phantom in FIG. 3, the slope of the upper frame surface 12 may be 30°.

Mounted on the frame adjacent the forward end of the upper frame surface 12 is a knee support 46. Knee support 46 is comprised of a padded non-slip element which extends substantially across the width of the upper frame surface 12. The knee support is carried by an L-shaped rigid support having an upper relatively horizontal surface member 48 and a downwardly extending member 50. An elongated slot 52 is formed in the member 48. A bolt 54 extends upwardly through the upper frame surface 12 and through the slot 52 and terminates in a washer 56 and a wing nut 58. Loosening the wing nut 58 allows the knee support to be moved forwardly or backwardly as desired and is then locked into place by tightening the wing nut 58.

Also mounted on the upper surface of the upper inclined frame member 12 are a plurality of rollers. In the preferred embodiment, four such rollers are utilized. Rollers 60 and 62 are mounted in line with each other adjacent the left edge and rollers 64 and 66 are similarly mounted at the front and back of the upper frame surface adjacent the right edge thereof. Also carried by the upper frame surface 12 and rigidly secured thereto is a raised stop member 68.

A movable body support means 70 is carried by the frame and particularly the upper frame surface 12. The body support means includes a pair of elongated rigid planar panels 72 and 74 which are hinged together at their forward ends by hinges 76. The panel members 72 and 74 are movable between the collapsed position shown in FIG. 1 and the open position shown in FIGS. 2 and 3. The panels are maintained in the open position by upright member 78 which is hinged at 80 to the lower panel 74. In its raised position, the upright member 78 rests in the groove formed between the stop member 82 and the undersurface of the panel 72. As shown in FIG. 1, the upright member 78 can pivot rearwardly when it is desired to collapse the panel 72 onto panel 74.

Figure 5:
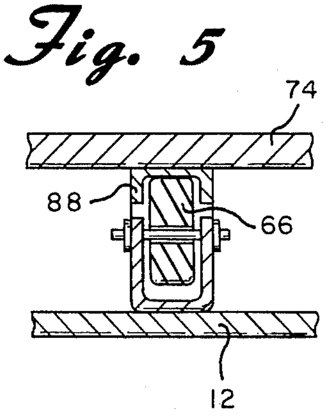
FIG. 5 is a cross-sectional view taken through the line 5—5 of FIG. 3.

The undersurface on the panel 74 carries a plurality of tracks such as shown at 84, 86, 88 and 90. Each track is associated with a different roller carried by the upper frame surface 12. As shown most clearly in FIGS. 3 and 5, the track 88 accommodates the roller 66 so that it can rotate freely therein. Thus, as a result of the cooperation between the rollers and the tracks, the body support means 70 moves relatively freely rearwardly and forwardly along the upper frame surface 12.

Figure 3:
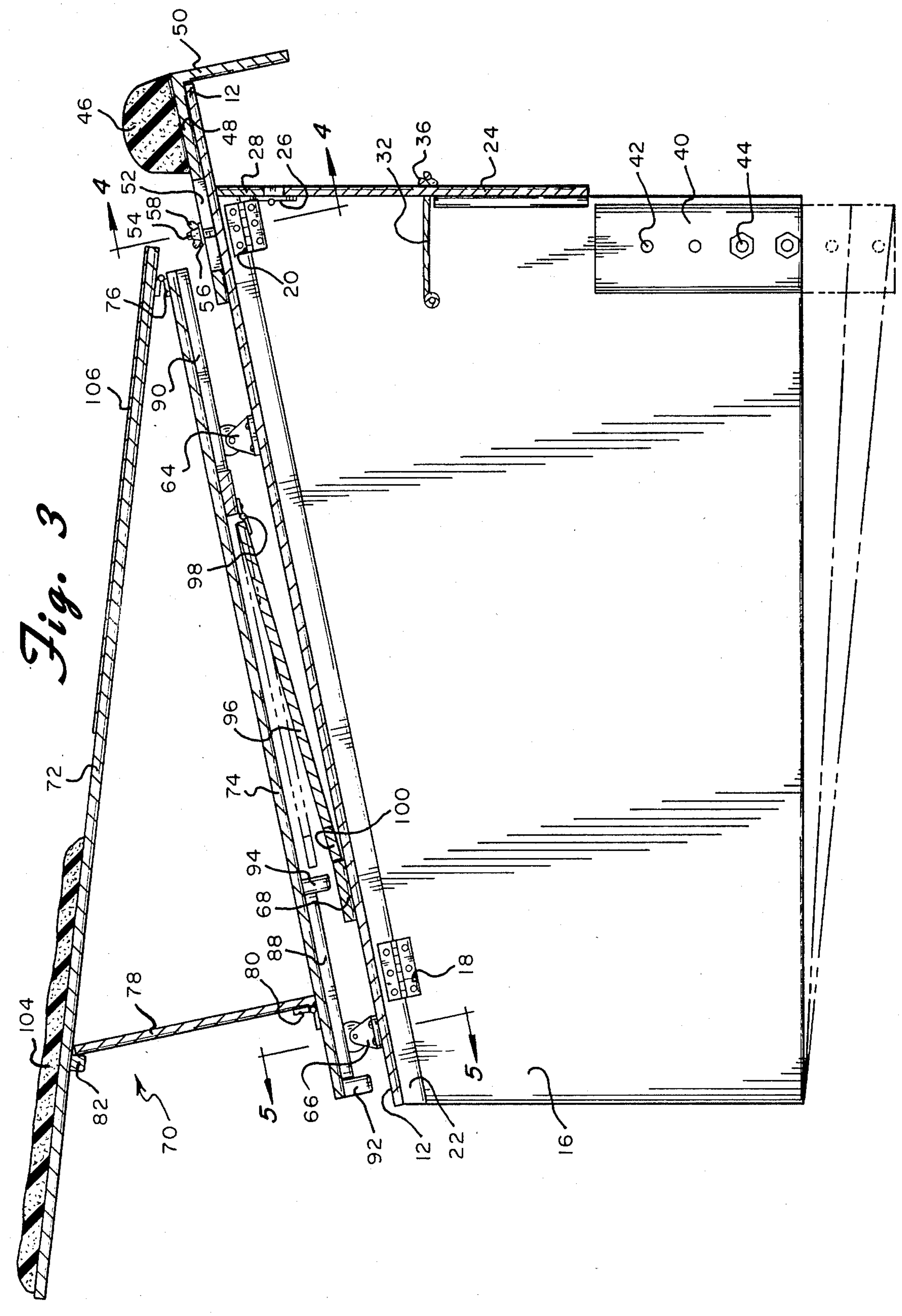
FIG. 3 is a cross-sectional view taken through the line 3—3 of FIG. 2.
Figure 4:
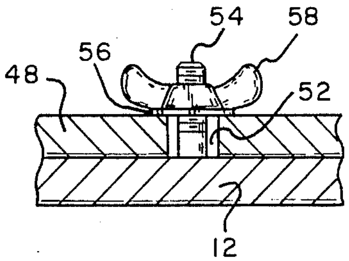
FIG. 4 is a cross-sectional view taken through the line 4—4 of FIG. 3.
Figure 6:
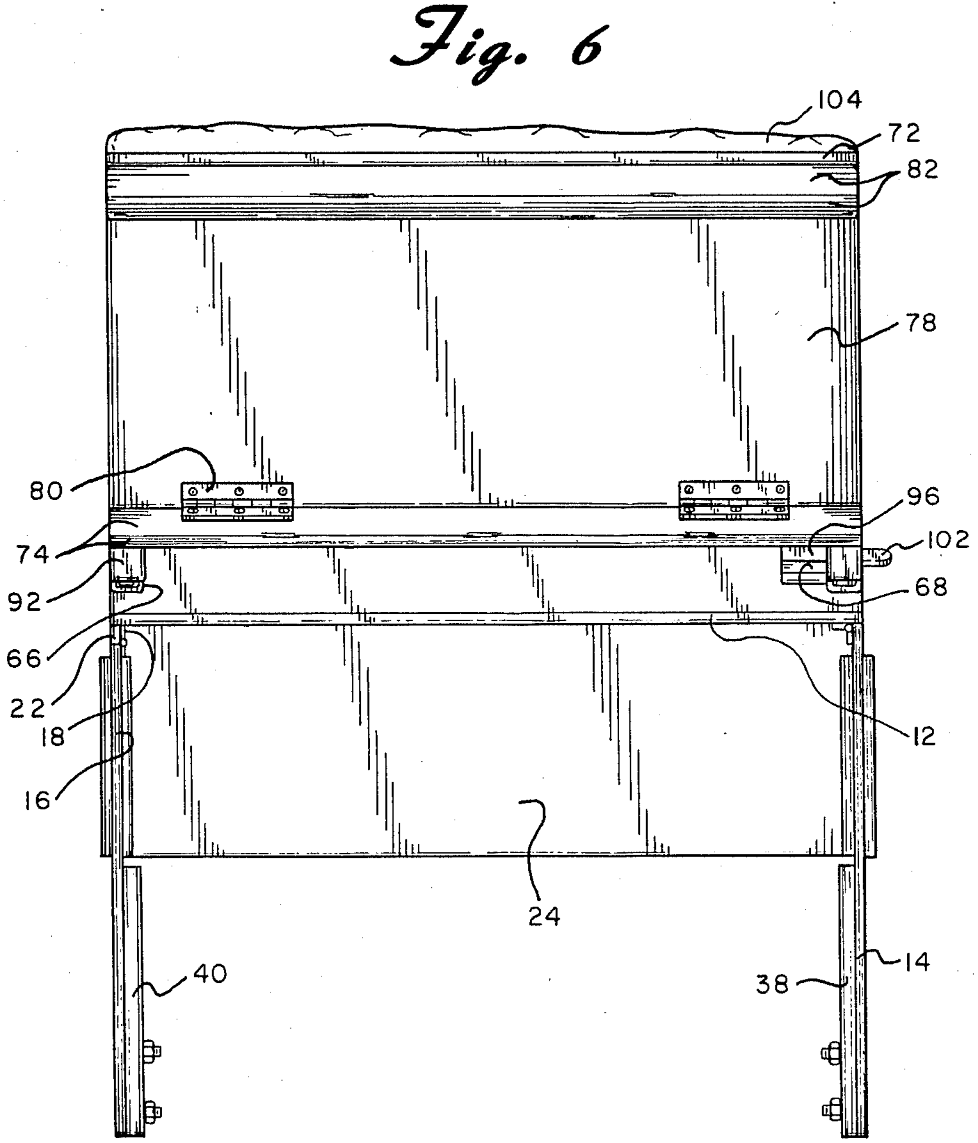
FIG. 6 is a cross-sectional view taken through the line 6—6 of FIG. 2.

In order to prevent the body support means from moving too far forwardly or rearwardly, at least the rear track means 84 and 88 include downwardly extending stop members such as shown at 92 and 94 in FIG. 3. These limit the movement of the body support means 70 to only about six inches. The lower panel member 74 also carries an elongated pawl 96 which is hinged at its forward end to the panel member 74 through hinge 98. The rearwardmost free end 100 of the pawl 96 is adapted to enage the stop member 68 mounted on the upper frame surface 12 to prevent rearward movement of the body support means 70. The pawl 96 is normally biased downwardly by the force of gravity into the position shown in full lines in FIG. 3. However, the pawl can be manually lifted through the use of handle 102 in order to bring the same into its upper position shown in phantom in FIG. 3. As can be seen most clearly from FIGS. 3 and 6, the handle 102 is located adjacent one side of the body support means near the middle thereof so as to be readily accessible to a person supported on the body support means.

The upper surface of the panel 72 is the body support surface and as shown in FIGS. 2 and 3 the body support surface extends substantially from a point adjacent the knee support 46 rearwardly and upwardly to an angle of between approximately 0° to about 30° above the horizontal. As should be readily apparent to those skilled in the art, the angle of inclination is adjusted by the feet 38 and 40 discussed above. The length of the body support surface is sufficient to underlie the upper thighs, buttocks, back and head of a person lying thereon. That portion of the body support surface which is intended to underlie the person's head and shoulders is padded and includes a non-slip surface such as shown at 104. The area of the body support surface between the non-slip padded area 104 and the lowermost end adjacent the knee support 46 and which is intended to underlie the person's buttocks includes a highly slippery surface 106 formed thereon.

The reclining traction lounge 10 described above functions in the following manner. In its collapsed form as shown in FIG. 1, the lounge is carried to its desired location and is then set up by unfolding the front wall 24 and the left and right side walls 14 and 16. These walls are then secured together as described above and the lounge 10 is placed upright on a floor or other support surface. The legs 38 and 40 are then adjusted to their proper position depending on the amount of traction desired. The greater extension of each of the legs 38 and 40, the greater the slope of the upper frame surface 12 and the greater the amount of traction.

After the frame is assembled, the body support means 70 is placed thereon with the rollers engaging the tracks. Panel 70 is pivoted upwardly and held in place by upright 78. A body support means is moved into its forward position as shown in FIG. 3 where the pawl 96 drops into place against the stop member 68. The knee support 46 is then adjusted to its proper position depending on the height of the person utilizing the lounge 10.

With the entire lounge 10 assembled as described, the person desiring to use the same lies with his back on the body support surface of the upper panel 72. The person's head and shoulders rest on the non-slip pad 104, his buttocks lie on the slippery surface 106 and the underside of his knees overlie the knee support 46 with his lower legs hanging downwardly over the panel 50. At this time, the person lifts the pawl 96 by grasping and lifting the handle 102. With the pawl released from the stop means 68, the entire body support means 70 rolls down the inclined surface 12 several inches. Since the person's shoulders and head tend to remain on the non-slip pad 104 and his knees are retained substantially in place by the knee support 46, his lower back tends to be stretched and placed in traction by the movement of the body support means 70 under his own weight. As pointed out above, the amount of traction is determined by the slope of the surface 12. By adjusting the feet 38 and 40, the slope of the body support surface on panel 72 is also adjusted to between approximately 0° to 30° above the horizontal. However, it is the slope of the surface 12 which determines the amount of traction rather than the slope of the body support surface.

The major components of the lounge 10 and particularly the walls and support surfaces of the frame and the panels of the body support means are preferably made of plywood or other strong rigid material. However, numerous different materials for all of the components of the invention could be utilized. The overall height of the lounge 10 is designed to be such that the person utilizing the same can easily lie on the same and get up without difficulty. Furthermore, while the frame is designed to be placed on the floor so that the lounge 10 is substantially self-contained, it could also be made substantially lower so that the frame could be supported on a sofa or bed or other similar surface.

The present invention may be embodied in other specific forms without departing from the spirit or essential attributes thereof and accordingly reference should be made to the appended claims rather than to the foregoing specification as indicating the scope of the invention.

I claim:

1. A reclining traction lounge comprising:

a frame having a front and a back and adapted to rest on the floor, said frame including an upper frame surface inclined downwardly from the front to the back at an angle of between approximately 10° to about 40' below the horizontal;

means carried by said frame adjacent the front of the upper frame surface for supporting a person's knees;

a body support means including a body support surface, said support surface being substantially planar and extending from a point adjacent said knee supporting means rearwardly and upwardly at an angle of between approximately 0° to about 30° above the horizontal, the length of said body support surface being sufficient to underlie the upper thighs, buttocks, back and head of a person lying thereon;

means, located between said body support means and said upper frame surface for allowing relatively free limited movement of said body support means rearwardly and forwardly along said upper frame surface, said body support means being movable relative to said knee supporting means;

means for temporarily maintaining said body support means in a forward position;

means for releasing said maintaining means to allow said body support means to move rearwardly while a person is lying on the lounge, said releasing means being located adjacent one side of said body support means so as to be readily accessible to and manually operable by said person lying on said lounge;

said body support surface having a padded non-slip surface formed thereon adjacent the upper portion thereof adapted to underlie the person's head and shoulders, said body support surface also having a slippery portion thereon in the area adapted to underlie the person's buttocks.

2. The invention as claimed in claim 1 wherein said frame is comprised of a plurality of parts hinged together so that the same can be collapsed for portability.

3. The invention as claimed in claim 1 including means for adjusting the angle of said upper frame surface.

4. The invention as claimed in claim 3 wherein said adjusting means are comprised of vertically adjustable feet for said frame.

5. The invention as claimed in claim 1 wherein the position of said knee supporting means is adjustable.

6. The invention as claimed in claim 1 wherein said means for allowing movement are comprised of rollers.

7. The invention as claimed in claim 6 wherein said rollers are mounted on said upper frame surface and wherein said body support means includes rails for engaging said rollers.

8. The invention as claimed in claim 1 wherein said means for temporarily maintaining said body support means in a forward position is comprised of a stop member carried by said upper frame surface and a movable pawl carried by said body support means and adapted to engage said stop member.

9. The invention as claimed in claim 8 wherein said pawl is normally biased in a position wherein it is adapted to engage said stop member.

10. The invention as claimed in claim 9 wherein said means for releasing includes a manually operable handle carried by said pawl.

* * * * *